(12) United States Patent
Heikenwälder et al.

(10) Patent No.: US 11,806,361 B2
(45) Date of Patent: Nov. 7, 2023

(54) TREATMENTS OF NON-ALCOHOLIC STEATOHEPATITIS (NASH)

(71) Applicant: DEUTSCHES KREBSFORSCHUNGSZENTRUM STIFTUNG DES ÖFFENTLICHEN RECHTS, Heidelberg (DE)

(72) Inventors: Mathias Heikenwälder, Heidelberg (DE); Lars Zender, Rottenburg (DE); Achim Weber, Zürich (CH)

(73) Assignee: DEUTSCHES KREBSFORSCHUNGSZENTRUM STIFTUNG DES ÖFFENTLICHEN RECHTS, Heidelberg (DE)

( * ) Notice: Subject to any disclaimer, the term of this patent is extended or adjusted under 35 U.S.C. 154(b) by 153 days.

(21) Appl. No.: 17/218,682

(22) Filed: Mar. 31, 2021

(65) Prior Publication Data
US 2021/0213042 A1 Jul. 15, 2021

Related U.S. Application Data

(62) Division of application No. 16/307,643, filed as application No. PCT/EP2017/066025 on Jun. 28, 2017, now Pat. No. 11,052,102.

(30) Foreign Application Priority Data

Jun. 28, 2016 (EP) ..................... 16176755

(51) Int. Cl.
| | |
|---|---|
| C07H 21/02 | (2006.01) |
| C07H 21/04 | (2006.01) |
| A61K 31/7105 | (2006.01) |
| A61P 1/16 | (2006.01) |
| A61K 9/00 | (2006.01) |
| A61K 31/192 | (2006.01) |
| A61K 31/405 | (2006.01) |
| A61K 31/616 | (2006.01) |
| C12N 15/113 | (2010.01) |
| A61K 31/713 | (2006.01) |
| A61K 31/00 | (2006.01) |

(52) U.S. Cl.
CPC ........ *A61K 31/7105* (2013.01); *A61K 9/0014* (2013.01); *A61K 9/0019* (2013.01); *A61K 9/0053* (2013.01); *A61K 31/00* (2013.01); *A61K 31/192* (2013.01); *A61K 31/405* (2013.01); *A61K 31/616* (2013.01); *A61K 31/713* (2013.01); *A61P 1/16* (2018.01); *C12N 15/113* (2013.01); *C12N 2310/11* (2013.01); *C12N 2310/20* (2017.05)

(58) Field of Classification Search
CPC ........... C12N 2310/11; C12N 15/113
See application file for complete search history.

(56) References Cited

U.S. PATENT DOCUMENTS

| | | |
|---|---|---|
| 2011/0082119 A1 | 4/2011 | Yano |
| 2011/0212543 A1 | 9/2011 | Patzk |

FOREIGN PATENT DOCUMENTS

WO 2009008539 A1 1/2009

OTHER PUBLICATIONS

Kurreck et al. (Nucleic Acids Research, 2002, 30, 9, 1911-1918).*
Albers, C. A. et al., "Exome sequencing identifies NBEAL2 as the causative gene for gray platelet syndrome." Nature Genetics 43(8):735-737, Jul. 2011.
Chen, J. et al., "Celecoxib attenuates liver steatosis and inflammation in non-alchoholic steatohepatitis induced by high-fat diet in rats." Molecular Medicine Reports, Feb. 2011, 4: 811-816.
Fujita, K. et al., "Effectiveness of antiplatelet drugs against experimental non-alcoholic fatty liver disease." British Medical Association, Jul. 2008, 6-8.
Fujita, K. et al., "Novel therapeutic approach for NAFLD using antiplatelet agents in an animal model." Hepatology, Oct. 2007, 46(4): 762A-763A.
Hickman I. J. et al., "Altered clot kinetics in patients with non-alcoholic fatty liver disease." Annals of Hepatology, Dec. 2009, 8(4): 331-338.
Jiang, Z. Gordon et al., "Aspirin use is associated with lower indices of liver fibrosis among adults in the United States." Alimentary Pharmacology and Therapeutics, Jan. 2016, 43(6): 734-743.
Madrigal-Perez, Violeta M et al., "Preclinical analysis of nonsteroidal anti-inflammatory drug usefulness for the simultaneous prevention of steatohepatitis, atherosclerosis and hyperlipidemia." Int J Clin Exp Med, Dec. 2015, 8(12): 22477-22483.
Musso, G et al., "Non-alcoholic steatohepatitis: emerging molecular targets and therapeutic stratagies." Nature Reviews, Jan. 2016, 15(4): 249-274.
Northup P. G. et al., "Hypercoagulation and Thrombophilia in Nonalcoholic Fatty Liver Disease: Mechanisms, Human Evidence, Therapeutic Implications, and Preventative Implications." Seminars in Liver Disease, Feb. 2012, 32(1): 39-48.
Papatheodoridis, George V., et al., "Thrombotic risk factors and liver histologic lesions in non-alcoholic fatty liver disease." Journal of Hepatology, Aug. 2009, 51(5): 931-938.

(Continued)

*Primary Examiner* — Amy H Bowman
(74) *Attorney, Agent, or Firm* — SALIWANCHIK, LLOYD & EISENSCHENK

(57) ABSTRACT

The present invention provides novel compounds that target thrombocyte activity or aggregation capacity through cellular components for the treatment of diseases associated with Non-Alcoholic Fatty Liver Disease (NAFLD). The invention provides these compounds for treating non-alcoholic steatohepatitis (NASH), a progressed stage of NAFL (non-alcoholic fatty liver), in order to avoid the development of liver cirrhosis and Hepatocellular Carcinoma (HCC). Further provided are pharmaceutical compositions, comprising the compounds of the invention, and methods for screening new NASH therapeuticals.

11 Claims, 16 Drawing Sheets

(56) References Cited

OTHER PUBLICATIONS

Singhal, R et al., "Hemoglobin interaction with GP1b induces platelet activation and apoptosis: a novel mechanism associated with intravascular hemolysis." The Hematology Journal: Official Organ of the European Hematology Association, Sep. 2015, 100(12): 1526-1533.
Tripodi, A et al., "Procoagulant imbalance in patients with non-alcoholic fatty liver disease." Journal of Hepatology, Mar. 2014, 61(1): 148-154.
Zein C. O. et al., "Pentoxifylline improves nonalcoholic steatohepatitis: A randomized placebo-controlled trial." Hepatology, Aug. 24, 2011, 54(5): 1610-1619.
Cauwenberghs, Nancy et al. "Antithrombotic Effect of Platelet Glycoprotein lb-Blocking Monoclonal Antibody Fab Fragments in Nonhuman Primates," Arterioscler Thromb Vasc Biol., vol. 20, No. 5, pp. 1347-1353, May 2000.

* cited by examiner

A

B

C

TREATMENTS OF NON-ALCOHOLIC STEATOHEPATITIS (NASH)

CROSS REFERENCE TO RELATED APPLICATIONS

This application is a Divisional application of co-pending application U.S. Ser. No. 16/307,643, filed Dec. 6, 2018; which is a National Stage Application of International Application Number PCT/EP2017/066025, filed Jun. 28, 2017; which claims priority to European Patent Application No. 16176755.3, filed Jun. 28, 2016.

FIELD OF THE INVENTION

The present invention provides novel compounds that target thrombocyte activity or aggregation capacity through cellular components for the treatment of diseases associated with Non-Alcoholic Fatty Liver Disease (NAFLD). The invention provides these compounds for treating non-alcoholic steatohepatitis (NASH), a progressed stage of NAFL (non-alcoholic fatty liver), in order to avoid the development of liver cirrhosis and Hepatocellular Carcinoma (HCC). Further provided are pharmaceutical compositions, comprising the compounds of the invention, and methods for screening new NASH therapeuticals.

BACKGROUND OF THE INVENTION

Changes in life-style over the last decades such as high caloric intake (e.g. through high fat, high fructose and high glucose diet) combined with sedentary life style have increased the incidence of overweight and metabolic syndrome, which is characterized by abdominal obesity, insulin resistance, hypertonia and dyslipidemia. The latest WHO cancer report predicts a doubling in cancer incidence within the next two decades, whereof the great majority will be attributable to modifiable risk factors such as high caloric intake, smoking and sedentary lifestyle (Stewart and Wild, 2014). A strong link between obesity and cancer incidence is well-established and a body mass index (BMI)>25 substantially increases the risk to develop several cancers (Calle and Kaaks, 2004). The liver, which is the most important metabolic organ of the body, is strongly affected by a chronic state of hypercaloric uptake, overweight, sedentary lifestyle and the resulting pathology (metabolic syndrome).

Non-alcoholic fatty liver disease (NAFLD), comprising several liver diseases including NAFL and NASH, which is the most frequent liver disease world-wide, is a clinical manifestation of overweight and metabolic syndrome. NAFL is a chronic disease that can last several decades and is characterized by predominant macrovesicular steatosis of the liver. The prevalence of NAFL is increasing globally (Loomba et al., 2013). Currently, 90 million Americans and 40 million Europeans suffer from NAFLD. Interestingly, also developing countries show a strong rise in NAFLD cases, reflecting the consequences of industrialization and a concomitant "Western life style". A significant number of NAFL patients develop non-alcoholic steatohepatitis (NASH), fibrosis and subsequently hepatocellular carcinoma (HCC). At the same time, the amount of people suffering from NASH is increasing in the USA and Europe. Consequently, obesity, steatosis and steatohepatitis have attracted increased attention due to rising HCC incidence in Western countries (White et al., 2012). In line, the most common etiology of HCC in industrialized countries is currently switching from chronic viral infections (e.g. Hepatitis B and C viruses) to obesity, making HCC the most rapidly increasing type of cancer in the U.S., with a similar trend observed in Europe (American Cancer Society, 2007).

Today, a detailed understanding of how chronic steatosis develops into NASH and what factors control NASH to HCC transition is still lacking. At the same time no efficient therapeutics exist to treat NASH and treatment options for late stage HCC are limited, prolonging the life span of patients for only 3 to 6 months (Villanueva et al., 2014). It becomes increasingly clear that a number of pathways are involved in the pathogenesis of NASH and its progression to advanced stages of liver disease. These pathways may vary in different cohorts of patients with NASH. Understanding which pathways play a role in the development of NASH and NASH driven HCC will be critical before launching treatment modalities. Indeed, NASH is associated with metabolic syndrome in most cases in the Western world, but can manifest also at a lower BMI, e.g. in Asian countries and many patients do not seem to have insulin resistance. These observations suggest that additional genetic factors are potentially involved in disease progression (Loomba et al., 2013).

Clearly there remains a significant unmet need for novel therapeutic approaches to target NASH progression into cirrhosis and HCC. The object of the present invention is therefore to provide novel treatment targets to this end.

BRIEF SUMMARY

The above problem is solved by altering the activation and aggregation potential of platelets in order to inhibit inflammation in the liver as well as their deleterious effect on hepatocyte metabolism in the context of a high calorie diet. The invention therefore provides in a first aspect an inhibitor of thrombocytes for use in the treatment or prevention of a non-alcoholic fatty liver disease (NAFLD).

BRIEF DESCRIPTION OF THE DRAWINGS

The present invention will now be further described in the following examples with reference to the accompanying figures and sequences, nevertheless, without being limited thereto. For the purposes of the present invention, all references as cited herein are incorporated by reference in their entireties. In the Figures.

DETAILED DISCLOSURE

Figure 1:
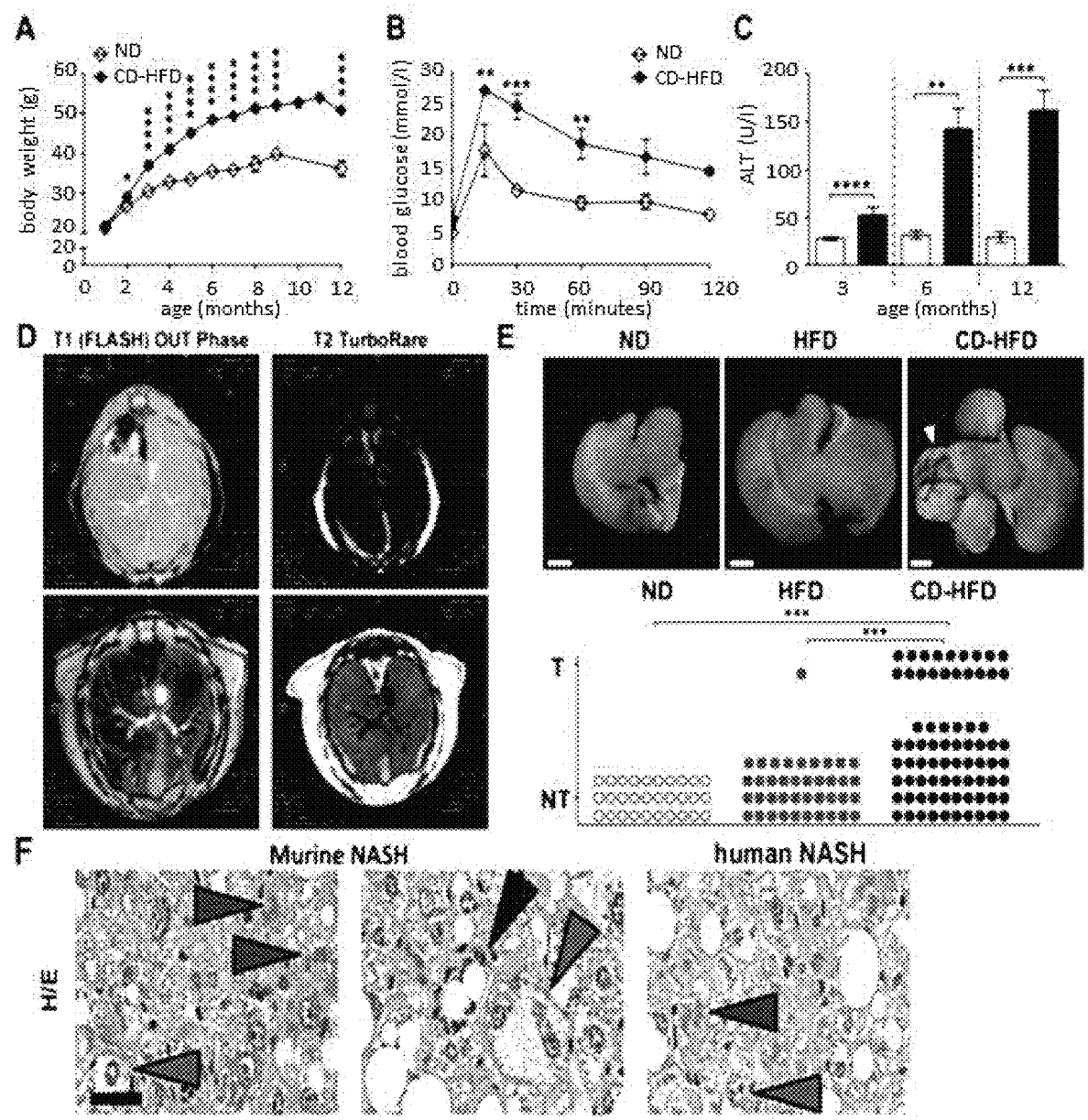
FIG. 1: Cholesterol Diet—High Fat Diet (CD-HFD) in mice recapitulates human NASH and NASH triggered HCC pathology

A thrombocyte inhibitor in context of the invention is also referred to as an antiplatelet drug or platelet aggregation inhibitor, and may be selected from any agent known in the art to inhibit the activity, proliferation or aggregation of thrombocytes. Examples of such compounds are agents that inhibit platelet function by inhibiting the aggregation, or by adhesion or granular secretion of platelets. Anti-platelet agents used in context of the invention include, but are not limited to, the various known non-steroidal anti-inflammatory drugs (NSAIDS) such as aspirin, ibuprofen, naproxen, sulindac, indomethacin, mefenamate, droxicam, diclofenac, sulfinpyrazone, piroxicam, and pharmaceutically acceptable salts or prodrugs thereof. In another embodiment, the anti-platelet agent is an IIb/IIIa antagonists (e.g., tirofiban, eptifibatide, and abciximab), thromboxane-A2-receptor antagonists (e.g., ifetroban), thromboxane-A2-synthetase inhibitors, PDE-III inhibitors (e.g., dipyridamole), and pharmaceutically acceptable salts or prodrugs thereof. In another embodiment, the term anti-platelet agents (or platelet inhibitory agents), refers to ADP (adenosine diphosphate) receptor antagonists, which is in one embodiment, an antagonists of the purinergic receptors $P_2$ Yi and $P_2$ Yn—In one embodiment, $P_2$ $Yi_2$ receptor antagonists is ticlopidine, clopidogrel, or their combination and pharmaceutically acceptable salts or prodrugs thereof.

In some preferred embodiments of the invention, there is provided an inhibitor of inhibitor of Gp1b, GPV, GPIX, Factor 8, or Nbeal2 for use in the treatment or prevention of a non-alcoholic fatty liver disease (NAFLD). The above protein denominations are used for the following protein names in parenthesis Gp1b (Glycoprotein Ib), GpV (Glycoprotein V), GPIX (Glycoprotein IX), Factor 8 (or Factor VIII; FVIII), and Nbeal2 (Neurobeachin-like protein 2).

An "inhibitor of Gp1b, GPV, GPIX, Factor 8, or Nbeal2" is an antagonist of a mammalian homologue of Gp1b, GPV, GPIX, Factor 8, or Nbeal2 respectively, preferably human Gp1b, GPV, GPIX, Factor 8, or Nbeal2. As used herein, the term "inhibitor of Gp1b, GPV, GPIX, Factor 8, or Nbeal2" means a substance that affects a decrease in the amount or rate of Gp1b, GPV, GPIX, Factor 8, or Nbeal2 expression or activity. Such a substance can act directly, for example, by binding to Gp1b, GPV, GPIX, Factor 8, or Nbeal2 and decreasing the amount or rate of Gp1b, GPV, GPIX, Factor 8, or Nbeal2 expression or activity. A Gp1b, GPV, GPIX, Factor 8, or Nbeal2-antagonist can also decrease the amount or rate of Gp1b, GPV, GPIX, Factor 8, or Nbeal2 expression or activity, for example, by binding to Gp1b, GPV, GPIX, Factor 8, or Nbeal2 in such a way as to reduce or prevent interaction of Gp1b, GPV, GPIX, Factor 8, or Nbeal2 with a ligand; by binding to Gp1b, GPV, GPIX, Factor 8, or Nbeal2 and modifying it, such as by removal or addition of a moiety; and by binding to Gp1b, GPV, GPIX, Factor 8, or Nbeal2 and reducing its stability. A Gp1b, GPV, GPIX, Factor 8, or Nbeal2-antagonist can also act indirectly, for example, by binding to a regulatory molecule or gene region so as to modulate regulatory protein or gene region function and affect a decrease in the amount or rate of Gp1b, GpV, GpIX, Factor 8, or Nbeal2 expression or activity. Thus, a Gp1b, GpV, GpIX, Factor 8, or Nbeal2-antagonist can act by any mechanisms that result in decrease in the amount or rate of Gp1b, GpV, GpIX, Factor 8, or Nbeal2 expression, stability or activity.

A Gp1b, GpV, GpIX, Factor 8, or Nbeal2-antagonist can be, for example, a naturally or non-naturally occurring macromolecule, such as a polypeptide, peptide, peptidomimetic, nucleic acid, carbohydrate or lipid. A Gp1b, GpV, GpIX, Factor 8, or Nbeal2-antagonist further can be an antibody, or antigen-binding fragment thereof, such as a mono-clonal antibody, humanized antibody, chimeric antibody, minibody, bifunctional antibody, single chain antibody (scFv), variable region fragment (Fv or Fd), Fab or F(ab)2. A Gp1b, GpV, GpIX, Factor 8, or Nbeal2-antagonist can also be polyclonal antibodies specific for Gp1b, GpV, GpIX, Factor 8, or Nbeal2. A Gp1b, GpV, GpIX, Factor 8, or Nbeal2-antagonist further can be a partially or completely synthetic derivative, analog or mimetic of a naturally occurring macromolecule, or a small organic or inorganic molecule.

A Gp1b, GpV, GpIX, Factor 8, or Nbeal2-antagonist that is an antibody can be, for example, an antibody that binds to Gp1b, GpV, GpIX, Factor 8, or Nbeal2 and inhibits binding to a Gp1b, GpV, GpIX, Factor 8, or Nbeal2 ligand, or alters the activity of a molecule that regulates Gp1b, GpV, GpIX, Factor 8, or Nbeal2 expression or activity, such that the amount or rate of Gp1b, GpV, GpIX, Factor 8, or Nbeal2 expression or activity is decreased. An antibody useful in a method of the invention can be a naturally occurring antibody, including a monoclonal or polyclonal antibodies or fragment thereof, or a non-naturally occurring antibody, including but not limited to a single chain antibody, chimeric antibody, bifunctional antibody, complementarity determining region-grafted (CDR-grafted) antibody and humanized antibody or an antigen-binding fragment thereof.

A Gp1b, GpV, GpIX, Factor 8, or Nbeal2-antagonist that is a nucleic acid can be, for example, an anti-sense nucleotide sequence, an RNA, DNA, RNA/DNA, or LNA molecule, or an aptamer sequence. An anti-sense nucleotide sequence can bind to a nucleotide sequence within a cell and modulate the level of expression of Gp1b, GpV, GpIX, Factor 8, or Nbeal2, respectively, or modulate expression of another gene that controls the expression or activity of Gp1b, GpV, GpIX, Factor 8, or Nbeal2. Similarly, an RNA molecule, such as a catalytic ribozyme, can bind to and alter the expression of a Gp1b, GpV, GpIX, Factor 8, or Nbeal2 gene, or other gene that controls the expression or activity of Gp1b, GpV, GpIX, Factor 8, or Nbeal2. An aptamer is a nucleic acid sequence that has a three dimensional structure capable of binding to a molecular target.

A Gp1b, GpV, GpIX, Factor 8, or Nbeal2-antagonist that is a nucleic acid also can be a double-stranded RNA molecule for use in RNA interference methods. RNA interference (RNAi) is a process of sequence-specific gene silencing by post-transcriptional RNA degradation, which is initiated by double-stranded RNA (dsRNA) homologous in sequence to the silenced gene. A suitable double-stranded RNA (dsRNA) for RNAi contains sense and antisense strands of about 21 contiguous nucleotides corresponding to the gene to be targeted that form 19 RNA base pairs, leaving overhangs of two nucleotides at each 3' end (Elbashir et al., Nature 411:494-498 (2001); Bass, Nature 411:428-429 (2001); Zamore, Nat. Struct. Biol. 8:746-750 (2001)). dsRNAs of about 25-30 nucleotides have also been used successfully for RNAi (Karabinos et al., Proc. Natl. Acad. Sci. USA 98:7863-7868 (2001). dsRNA can be synthesized in vitro and introduced into a cell by methods known in the art. As already indicated, the antisense nucleic acid is an RNA interference inducing nucleic acid, preferably comprising a sequence complementary to a Gp1b, GpV, GpIX, Factor 8, or Nbeal2 mRNA sequence, such as, but not limited to, a siRNA, shRNA, miRNA, LNA-constructs. Such constructs are known in the art and easy to prepare by the skilled artisan.

Another option is furthermore the use of CRISPR/Cas9 or similar gene editing approaches to introduce mutations into the genes of Gp1b, GpV, GpIX, Factor 8, or Nbeal2. Such CRISPR gene editing constructs shall therefore be comprised by the term Gp1b, GpV, GpIX, Factor 8, or Nbeal2-antagonist insofar they are used to impair expression, stability or function of Gp1b, GpV, GpIX, Factor 8, or Nbeal2.

Preferred embodiments of the present invention pertain to non-alcoholic steatohepatitis (NASH) as NAFLD of the invention. Therefore, it is preferred in context of the invention that the treatment of NAFLD involves a patient group suffering from NASH and not NAFL, and therefore patients which already developed the more advanced form of a NAFLD. Therefore, the patient group preferable to be treated with the inhibitors of the invention are patients showing signs of fat and inflammation, sometimes also damage, in the liver. In some embodiments the patients to be treated in context of the invention are patients which do not suffer from signs of cirrhosis or hepatocellular carcinoma (HCC). Other embodiments however provide that patients to be treated in accordance with the invention already show signs of cirrhosis and/or HCC. Preferably the inhibitors of the invention are for use in a treatment which is a prevention of HCC in a NASH-patient at risk to develop cirrhosis and/or HCC.

A patient at risk of developing NAFLD (preferably NASH) in context of the invention is a preferred subject to benefit for the inhibitors for use of the invention. Such a risk patient is for example a diabetic patient, an obese patient, or a patient suffering from the metabolic syndrome or another metabolic disorder.

Most preferably the subject to be treated in context of the invention (patient group) does not have a condition selected from the following group consisting of alcoholic liver injury, drug-induced liver injury, chronic active hepatitis, cirrhosis, liver cancer, hepatic steatosis and hepatocyte apoptosis.

The present invention provides for alleviation or a reduced progression of the NAFLD to be treated, in particular NASH. Therefore, the invention provides a treatment of NAFLD preferably NASH. The inhibitors of the invention are preferably used to reduce, stall, or reverse progression of NASH into liver cirrhosis, and/or progression of NASH into hepatocellular carcinoma (HCC). Thus treatment in context of the invention is preferably an alleviation of NASH into a non-NASH state of NAFLD.

In another aspect of the invention there is provided a pharmaceutical composition for use in the treatment or prevention of a non-alcoholic fatty liver disease (NAFLD), as described herein above, the pharmaceutical composition comprising an inhibitor of thrombocytes or an inhibitor of Gp1b, GpV, GpIX, Factor 8, or Nbeal2 (as described herein above) and a pharmaceutically acceptable carrier and/or excipient.

As used herein the language "pharmaceutically acceptable carrier" is intended to include any and all solvents, solubilizers, fillers, stabilizers, binders, absorbents, bases, buffering agents, lubricants, controlled release vehicles, diluents, emulsifying agents, humectants, lubricants, dispersion media, coatings, antibacterial or antifungal agents, isotonic and absorption delaying agents, and the like, compatible with pharmaceutical administration. The use of such media and agents for pharmaceutically active substances is well-known in the art. Except insofar as any conventional media or agent is incompatible with the active compound, use thereof in the compositions is contemplated. Supplementary agents can also be incorporated into the compositions. In certain embodiments, the pharmaceutically acceptable carrier comprises serum albumin.

The pharmaceutical composition of the invention is formulated to be compatible with its intended route of administration. Examples of routes of administration include parenteral, e.g., intrathecal, intra-arterial, intravenous, intradermal, subcutaneous, oral, transdermal (topical) and transmucosal administration. Most preferably the route of administration is a route that directly targets the liver of a subject to be treated.

In therapeutic applications, compositions are administered to a patient already suffering from a NAFLD, as described, in an amount sufficient to cure or at least partially stop the symptoms of the disease and its complications. An appropriate dosage of the pharmaceutical composition is readily determined according to any one of several well-established protocols. For example, animal studies (for example on mice or rats) are commonly used to determine the maximal tolerable dose of the bioactive agent per kilogram of weight. In general, at least one of the animal species tested is mammalian. The results from the animal studies can be extrapolated to determine doses for use in other species, such as humans for example. What constitutes an effective dose also depends on the nature and severity of the disease or condition, and on the general state of the patient's health.

In prophylactic applications, compositions containing, for example Gp1b, GpV, GpIX, Factor 8, or Nbeal2 antagonists, are administered to a patient susceptible to or otherwise at risk of a hepatic disease. Such an amount is defined to be a "prophylactically effective" amount or dose. In this use, the precise amount depends on the patient's state of health and weight.

In both therapeutic and prophylactic treatments, the antagonist contained in the pharmaceutical composition can be administered in several dosages or as a single dose until a desired response has been achieved. The treatment is typically monitored and repeated dosages can be administered as necessary. Compounds of the invention may be administered according to dosage regimens established whenever inactivation of p1b, GpV, GpIX, Factor 8, or Nbeal2 is required.

The daily dosage of the products may be varied over a wide range from 0.01 to 1,000 mg per adult per day. Preferably, the compositions contain 0.01, 0.05, 0.1, 0.5, 1.0, 2.5, 5.0, 10.0, 15.0, 25.0, 50.0, 100, 250 and 500 mg of the active ingredient for the symptomatic adjustment of the dosage to the patient to be treated. A medicament typically contains from about 0.01 mg to about 500 mg of the active ingredient, preferably from 1 mg to about 100 mg of the active ingredient. An effective amount of the drug is ordinarily supplied at a dosage level from 0.0002 mg/kg to about 20 mg/kg of body weight per day, especially from about 0.001 mg/kg to 10 mg/kg of body weight per day. It will be understood, however, that the specific dose level and frequency of dosage for any particular patient may be varied and will depend upon a variety of factors including the activity of the specific compound employed, the metabolic stability, and length of action of that compound, the age, the body weight, general health, sex, diet, mode and time of administration, rate of excretion, drug combination, the severity of the particular condition, and the host undergoing therapy.

In the pharmaceutical compositions of the present invention for oral, sublingual, subcutaneous, intramuscular, intravenous, transdermal, local or rectal administration, the active principle, alone or in combination with another active principle, can be administered in a unit administration form, as a mixture with conventional pharmaceutical supports, to animals and human beings. Suitable unit administration forms comprise oral-route forms such as tablets, gel capsules, powders, granules and oral suspensions or solutions, sublingual and buccal administration forms, aerosols, implants, subcutaneous, transdermal, topical, intraperitoneal, intramuscular, intravenous, subdermal, transdermal, intrathecal and intranasal administration forms and rectal administration forms.

The appropriate unit forms of administration include forms for oral administration, such as tablets, gelatine capsules, powders, granules and solutions or suspensions to be taken orally, forms for sublingual and buccal administration, aerosols, implants, forms for subcutaneous, intramuscular, intravenous, intranasal or intraocular administration and forms for rectal administration.

In the pharmaceutical compositions of the present invention, the active principle is generally formulated as dosage units containing from 0.5 to 1000 mg, preferably from 1 to 500 mg, more preferably from 2 to 200 mg of said active principle per dosage unit for daily administrations.

When preparing a solid composition in the form of tablets, a wetting agent such as sodium laurylsulfate can be added to the active principle optionally micronized, which is then mixed with a pharmaceutical vehicle such as silica, gelatine, starch, lactose, magnesium stearate, talc, gum arabic or the like. The tablets can be coated with sucrose, with various polymers or other appropriate substances or else they can be treated so as to have a prolonged or delayed activity and so as to release a predetermined amount of active principle continuously.

A preparation in the form of gelatin capsules is obtained by mixing the active principle with a diluent such as a glycol or a glycerol ester and pouring the mixture obtained into soft or hard gelatine capsules.

A preparation in the form of a syrup or elixir can contain the active principle together with a sweetener, which is preferably calorie-free, methyl-paraben and propylparaben as an antiseptic, a flavoring and an appropriate color.

The water-dispersible powders or granules can contain the active principle mixed with dispersants or wetting agents, or suspending agents such as polyvinylpyrrolidone, and also with sweeteners or taste correctors.

Rectal administration is effected using suppositories prepared with binders which melt at the rectal temperature, for example cacao butter or polyethylene glycols.

Parenteral, intranasal or intraocular administration is effected using aqueous suspensions, isotonic saline solutions or sterile and injectable solutions which contain pharmacologically compatible dispersants and/or wetting agents, for example propylene glycol, butylene glycol, or polyethylene glycol.

Thus a co-solvent, for example an alcohol such as ethanol or a glycol such as polyethylene glycol or propylene glycol, and a hydrophilic surfactant such as Tween® 80, can be used to prepare an aqueous solution injectable by intravenous route. The active principle can be solubilized by a triglyceride or a glycerol ester to prepare an oily solution injectable by intramuscular route.

Transdermal administration is effected using multilaminated patches or reservoirs into which the active principle is in the form of an alcoholic solution.

Administration by inhalation is effected using an aerosol containing for example sorbitan trioleate or oleic acid together with trichlorofluoromethane, dichlorotetrafluoroethane or any other biologically compatible propellant gas.

The active principle can also be formulated as microcapsules or microspheres, optionally with one or more carriers or additives.

Among the prolonged-release forms which are useful in the case of chronic treatments, implants can be used. These can be prepared in the form of an oily suspension or in the form of a suspension of microspheres in an isotonic medium.

The above problem is furthermore solved by a method for identifying whether a compound has an activity towards a treatment of NAFLD, preferably NASH (and referring to the particular medical indications as described above) the method comprising contacting a cell expressing a protein selected from the group consisting of Gp1b, GpV, GpIX, Factor 8, or Nbeal2, with a candidate compound, determining the expression, stability and/or activity of said protein compared to a control cell expressing the protein and which is not contacted with the candidate compound, wherein a reduced expression, stability and/or activity of the protein upon contacting with the candidate compound indicates that the candidate compound has an activity towards a treatment of NAFLD.

The candidate compound is preferably selected from antisense nucleic acid, CRISPR-Cas9 like gene editing construct, an antibody, or an antigen binding fragment thereof, a viral construct, a small molecule, a peptide, a ribozyme, or a recombinant protein. In general, for the screening method of the invention any potential inhibitor of Gp1b, GpV, GpIX, Factor 8, or Nbeal2 as defined herein, may be used as a candidate compound.

EXAMPLES

Example 1: The First Studied Mouse Model for Human NASH and Subsequent HCC Development Indeed that approach enabled the inventors to study a chronic model of NASH in the context of metabolic syndrome, triggering subsequent HCC in C57BL/6 mice, in the absence of chemical carcinogens or genetic mutations predisposing to NASH or HCC development. CD-HFD fed mice display several long term pathologies observed in human patients: abdominal obesity, overweight, insulin resistance, liver damage, production of reactive oxygen species (ROS) fibrosis, hepatic mitochondrial damage, dyslipidemia and NASH. Moreover, HCC developed 12 months post CD-HFD start and resembled histologically, genetically and morphologically human HCC (FIG. 1). Cholesterol Diet—High Fat Diet (CD-HFD) in mice recapitulates human NASH and NASH triggered HCC pathology. (FIG. 1A) Weight development in male normal diet fed (ND) and CD-HFD fed C57BL/6 mice. (FIG. 1B) Intraperitoneal Glucose tolerance test performed with 6-month-old male ND and CD-HFD C57BL/6 mice. (FIG. 1C) Quantification of serum aminotransferase (ALT) levels in male C57BL/6 mice reflecting liver damage. (FIG. 1D) MRI analyses on livers of 6-month-old ND and CD-HFD C57BL/6 mice. T1 (fast low-angle shot [FLASH]) OUT phase: dark color indicative of steatosis. T2 TurboRare visualizes increase in subcutaneous and abdominal fat and hepatic lipid accumulation (bright regions) in CD-HFD mice. (FIG. 1E) Macroscopy and histopathology of livers from 12-month-old ND, HFD, or CD-HFD C57BL/6 mice, with arrowhead pointing towards HCC. Scale bar: 5 mm. T: Tumor. NT: Non-Tumor. ***P=0.001. (F) Representative H&E staining of 12-month-old CD-HFD C57BL/6 livers and human livers illustrating NASH. Accumulation of Mallory Denk bodies (red arrowhead), ballooned hepatocytes (brown arrowhead), and satellitosis (blue arrowhead) is similar to human NASH pathology (right image). Scale bar: 50 µm.

The present mouse model, which recapitulates several pathophysiological aspects of human NASH, provides the basis for this invention and allows us to study the biology and development of NASH and NASH to HCC transition. Notably, using this mouse model it is demonstrated for the first time that CD8+ T-cells and NKT-cells become activated during metabolic syndrome, interact with hepatocytes via cytokines and alter hepatic lipid metabolism causing NASH and HCC. An identical profile of CD8+ and NKT cell activation was found in human NASH livers underlining the clinical relevance of our model (Wolf et al., Cancer Cell, 2014).

Opposing results have been published in the past in the frame of short-term in vivo experiments on the role of immune cells in experimentally induced NASH (Martin-Murphy et al., 2014; Lynch et al., 2012; Bhattacharjee et al., 2014). Notably, these models lacked a metabolic syndrome and were usually kept on a diet for only several weeks. In contrast, the present data, which are based on a long-term CD-HFD leading to obesity, metabolic syndrome and HCC in C57BL/6 mice, demonstrate that immune cells play an important role in triggering steatosis, NASH and NASH-driven HCC (Wolf et al., Cancer Cell, 2014). Moreover, the inventors could demonstrate that the inflammation profile of livers from CD-HFD mice looked similar to that of human NASH livers, e.g. as far as inflammatory cells in the liver or cytokine expression is concerned (FIG. 2).

Figure 2:
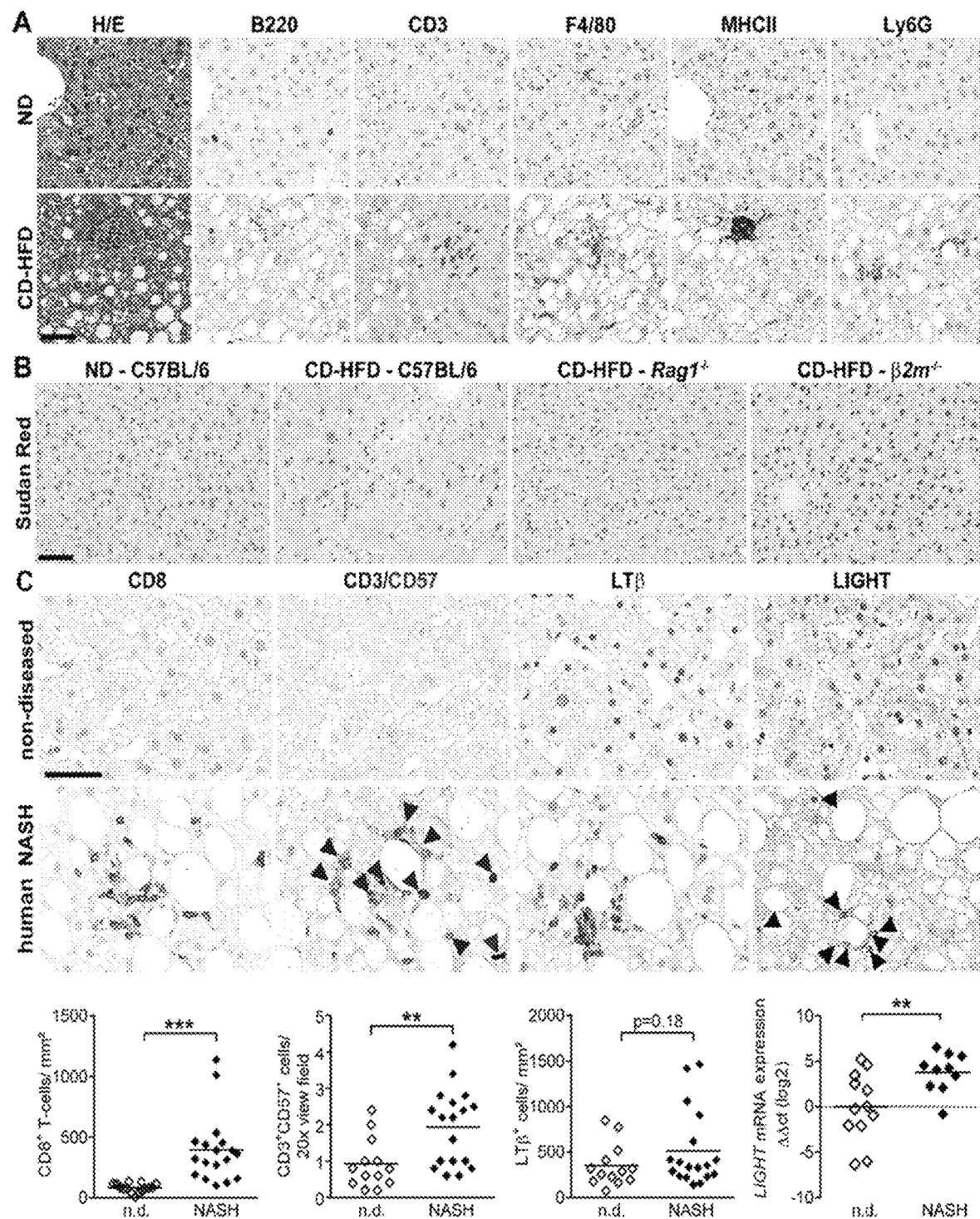
FIG. 2: CD-HFD recapitulates the inflammatory profile of human NASH.

In FIG. 2 from left to right: H&E, B220, CD3, F4/80, MHCII, and Ly6G. Inflammatory aggregates consisting of CD3+, F480+, and MHCII+ cells were observed. Scale bar: 50 µm. (B) CD8+ T and NKT cells control liver steatosis development. Sudan red staining of liver sections (12-month-old, indicated genotypes) demonstrated that depletion of B- and T-cells (Rag1−/− mice) or more specifically CD8+ and NKT cells (β2m−/− mice) sufficed to strongly reduce the development of steatosis upon CD-HFD. In line a reduction of other parameters such as aminotransferases, liver triglycerides is found (not shown). Scale bar: 50 µm. (C) Representative IHC of human non-diseased control livers and livers of NASH patients for CD8+ T cells, CD3+CD57+ NKT cells, LTβ and LIGHT expression with arrowheads indicating positive cells Scale bar: 50 µm. Densitometric analysis of immune cells and LIGHT expression analysed on mRNA level derived from human cryomaterial.

Example 2: Platelets are Increased, Activated and Aggregate in NASH

Figure 3:
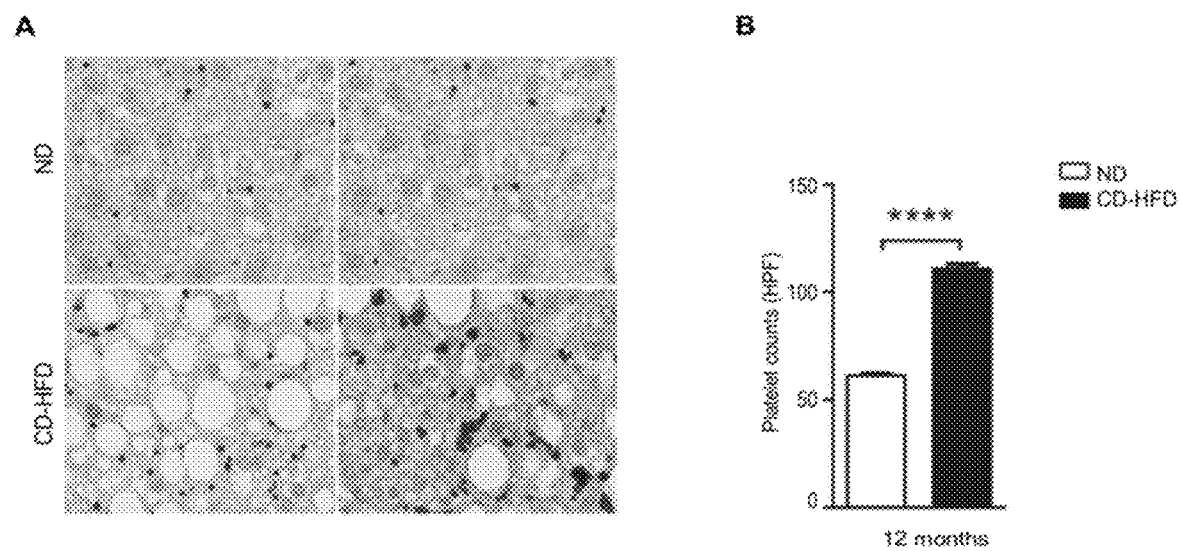
FIG. 3: Increase of platelets and aggregation as a sign of activation in the liver of mice suffering from NASH upon 6 months CD-HFD

FIG. 3 shows an increase of platelets and aggregation as a sign of activation in the liver of mice suffering from NASH upon 6 months CD-HFD. (FIG. 3A) Immunohistochemical images which identify platelets to aggregate and to be increased in number. Platelets are stained by GPIb. (FIG. 3B) Densitometric analysis of platelets show a strong and significant increase in number in the livers of CD-HFD treated mice. DATA NOT SHOWN: Similar images and a similar increase in GPIb numbers can be seen in patients suffering from NASH when compared to healthy patients.

Figure 4:
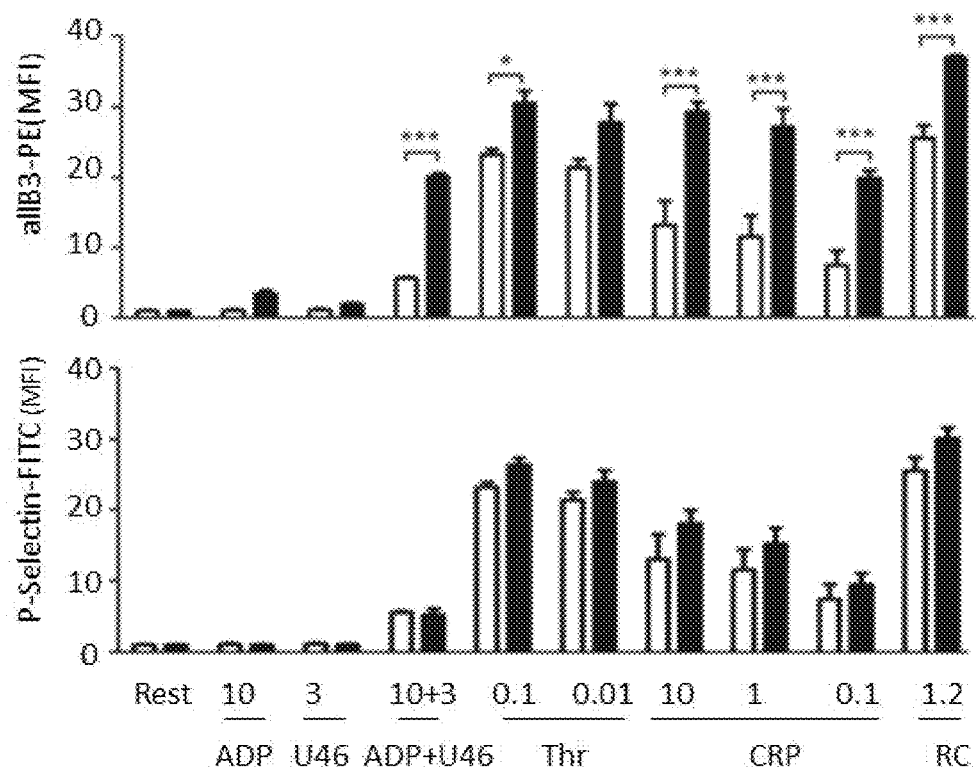
FIG. 4: Analysis of activation and accumulation capacity of platelets analysed by flow cytometry from peripheral blood

FIG. 4 shows an analysis of activation and accumulation capacity of platelets analysed by flow cytometry from peripheral blood. Flow cytometry analysis indicates that there is a significantly increased capacity of platelets to be activated (upper) and a tendency to aggregate (lower). By using different dilution curves of CRP or Thr a reproducible and consistent analysis of the platelet-response rate was visible.

Figure 5:
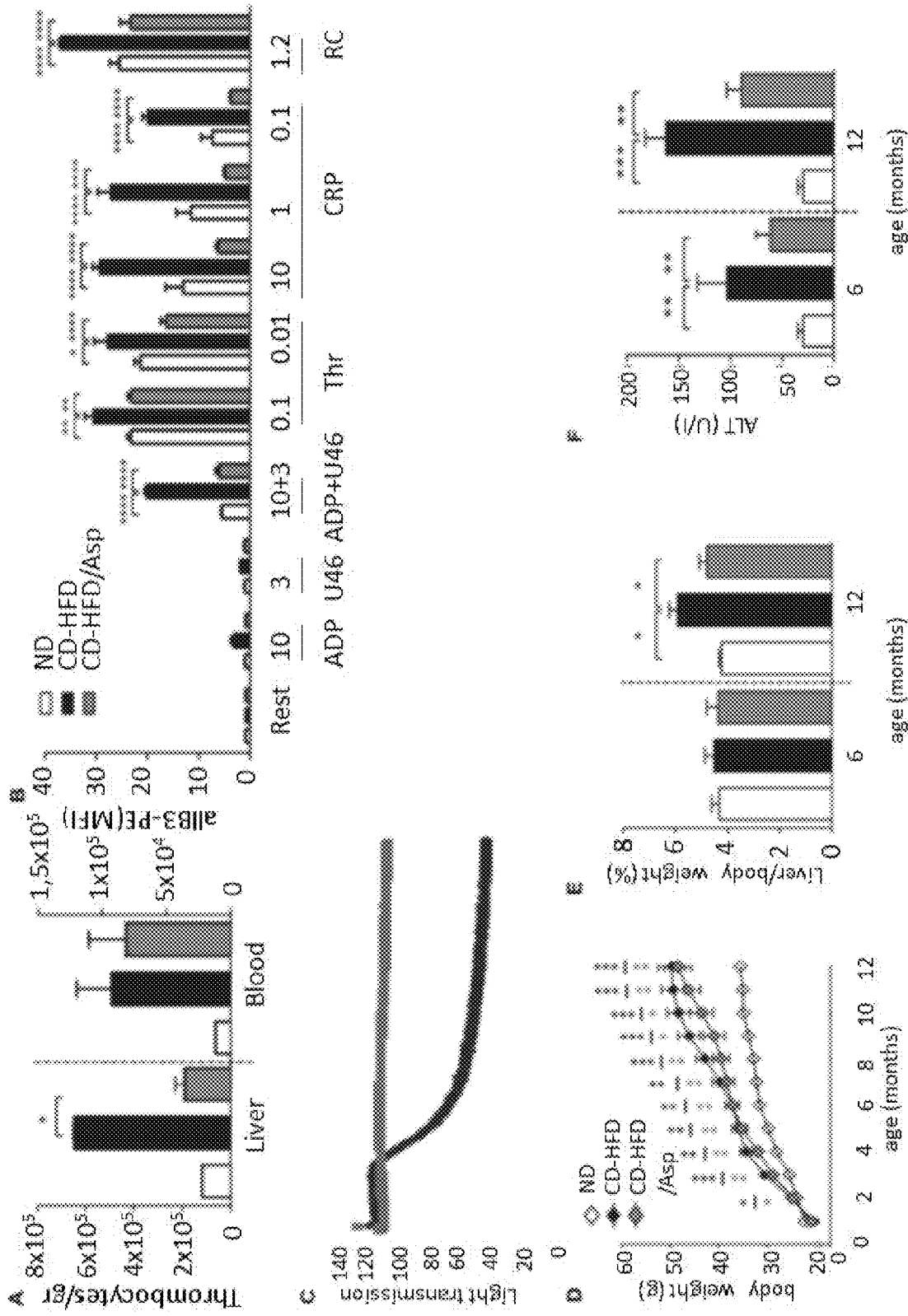
FIG. 5: Aspirin/Clopidrogrel (Asp/Clop), a thrombocyte aggregation inhibitor, treatment reduces the capacity of platelets aggregate and prevents NASH and aberrant hepatic lipid metabolism
Figure 5:
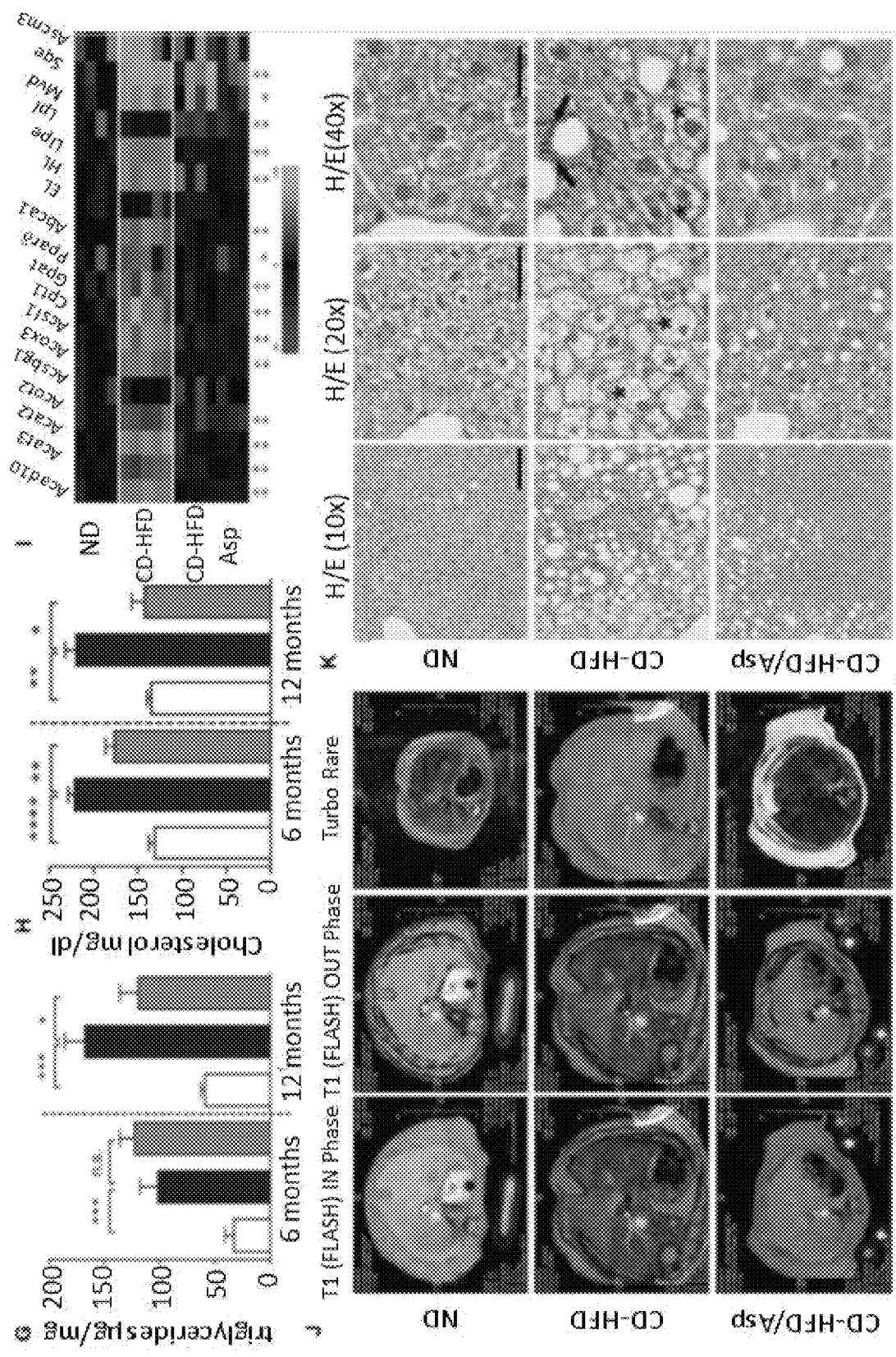

Aspirin/Clopidrogrel (Asp/Clop), a thrombocyte aggregation inhibitor, treatment reduces the capacity of platelets aggregate and prevents NASH and aberrant hepatic lipid metabolism (FIG. 5). (FIG. 5A) Asprin/Clopidrogrel treatment reduces the number of platelets in the liver (White bars: ND; Black bars: CD-HFD; Green bars: CD-HFD treated with Asp/Clop). (FIG. 5B) Activation status of platelets (investigated by an ex vivo assay) is significantly reduced upon Asp/Clop treatment on platelets taken from peripheral blood. (FIG. 5C) Aggregation capacity status (investigated by an ex vivo aggregation assay) of platelets is significantly reduced upon Asp/Clop treatment on platelets taken from peripheral blood. (FIG. 5D) Asp/Clop CD-HFD fed mice do develop obesity as CD-HFD mice. (FIG. 5E) Liver to body weight ratio is rescued upon Asp/Clop treatment at 12 months of age. (FIG. 5F) Liver damage as measured by ALT levels in serum is prevented in Asp/Clop treated mice. (FIG. 5G) Triglycerides are reduced in serum of Asp/Clop treated mice at 12 months of age. (FIG. 5H)

Serum cholesterol is reduced in Asp/Clop treated mice at 6 and 12 months, (FIG. 5I) Aberrant hepatic lipid metabolism and b-Oxidation is rescued in Asp/Clop treated mice—as analyzed by Real time PCR analysis for gene expression in the liver. Stars indicate significance. (FIGS. 5J and K) MRI analysis and histological analysis demonstrate that Asp/Clop treatment prevents the development of NASH. (FIG. 5J) Lipid deposition in the liver indicated by a dark staining in the T1 (FLASH) OUT phase is not detected—as in the CD-HFD. Still at the same time abdominal and subcutaneous fat are visible in Asp/Clop treated mice. (FIG. 5K) Histopathological signs of NASH (e.g. ballooned hepatocytes—see also stars) are absent in Asp/Clop treated mice.

Figure 6:
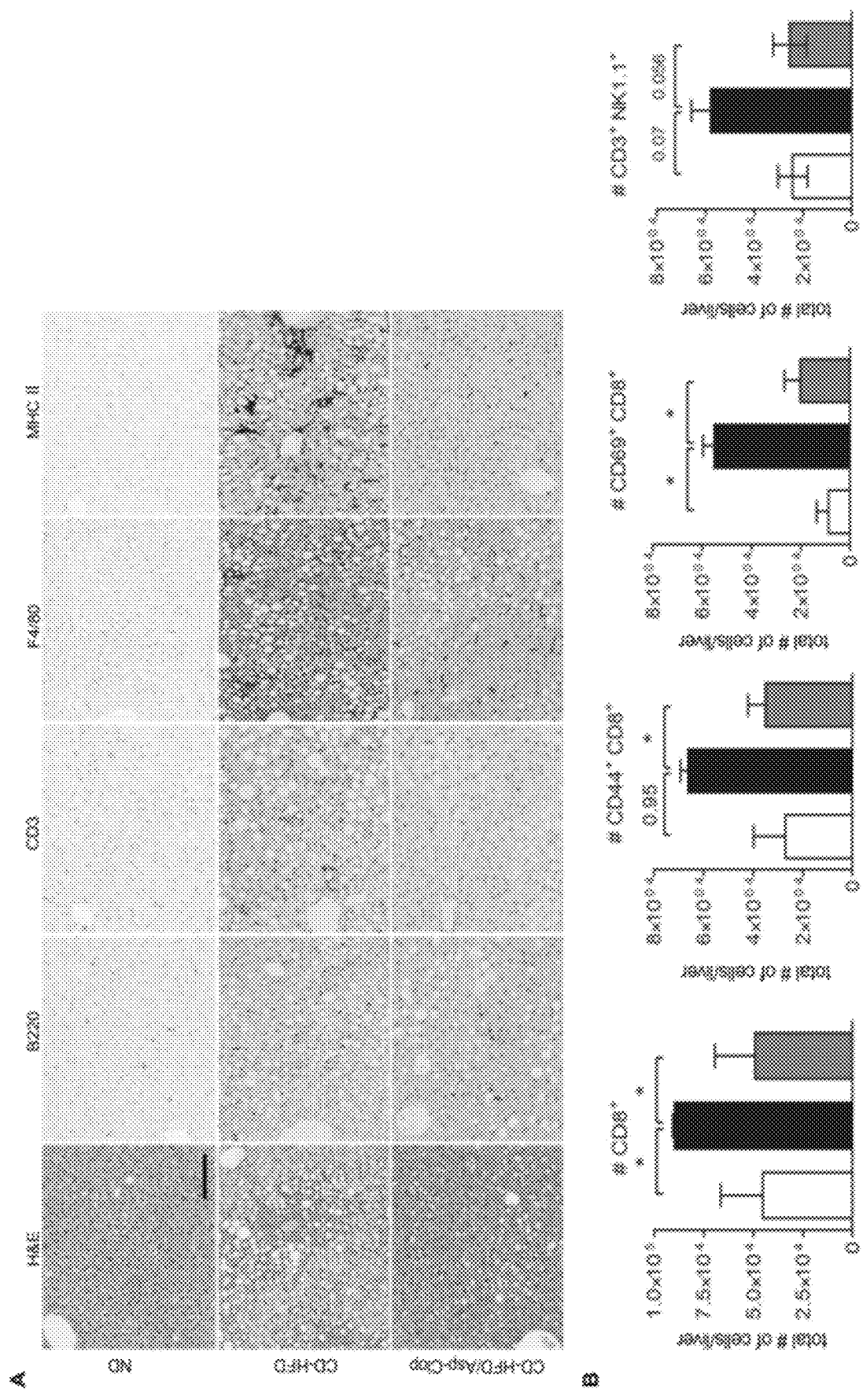
FIG. 6: Reduced amount of intrahepatic immune cells in Aps/Clp treated mice

Furthermore, a reduced amount of intrahepatic immune cells in Aps/Cip treated mice was observed (FIG. 6). (FIG. 6A) Reduction of several immune cell types including CD3+ T cells, F480+ cells and MHCII expressing cells. B220+ immune cells are not altered. Moreover, (FIG. 6B) flow cytometry analysis shows a significant reduction in the number of CD8+ T cells, the activation of CD44+CD8+ T cells, CD69+CD8+ T cells as well as in the number of CD3+NK1.1+ NKT cells (White bars: ND; Black bars: CD-HFD; Green bars: CD-HFD treated with Asp/Clop).

Figure 7:
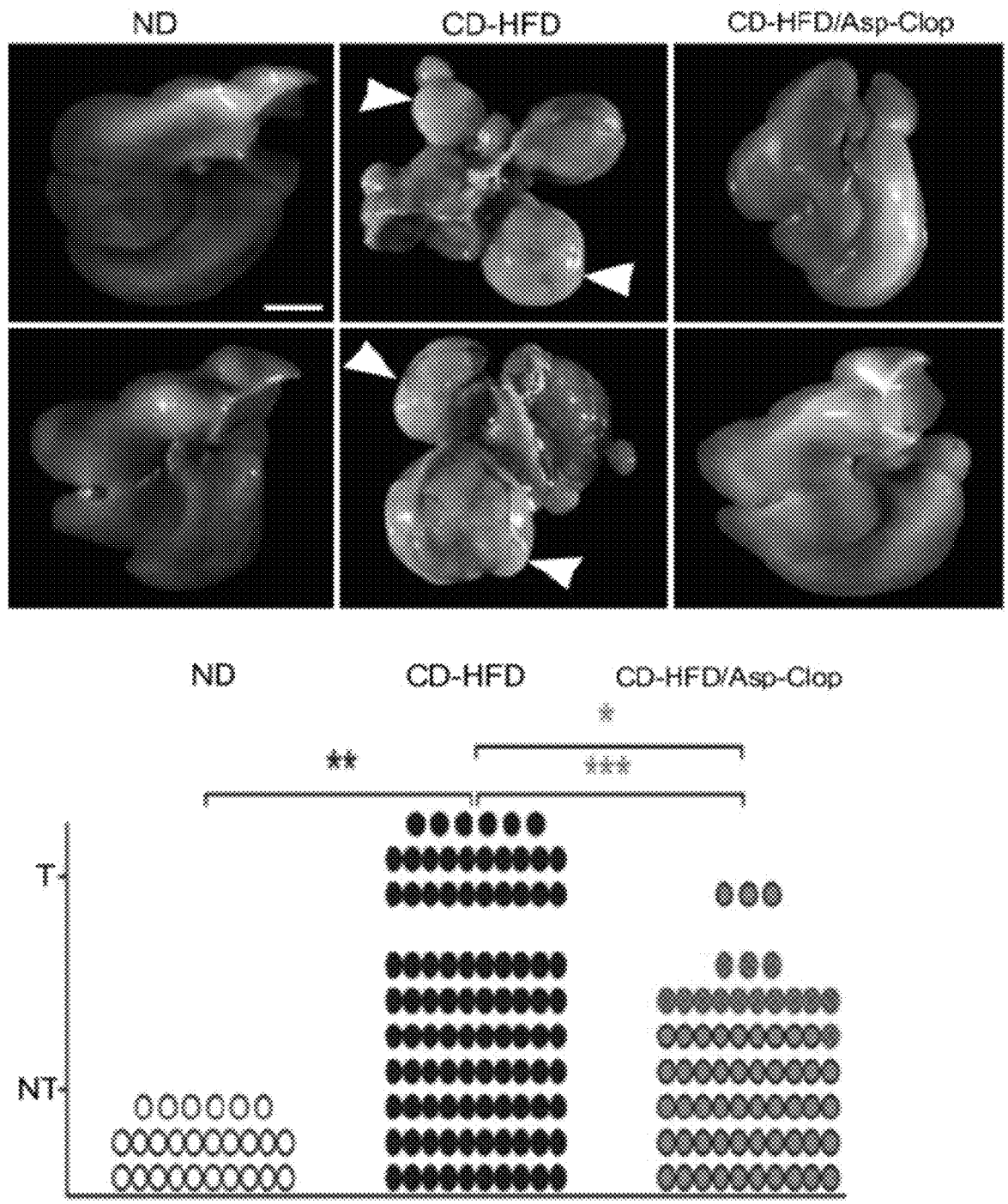
FIG. 7: Inhibiting the activity/aggregation of platelets reduces the number of HCC

Example 3: Inhibiting the Activity/Aggregation of Platelets Reduces the Number of HCC In the mouse model for NASH, the treatment with Asp/Clop resulted in the reduction in HCC incidence (FIG. 7). Significant reduction in the number of HCC in Asp/Clop treated mice. (White circles: ND; Black circles: CD-HFD; Green circles: CD-HFD treated with Asp/Clop low dose; red circles: Asp/Clop high dose).

Example 4: COX1, COX2 is not Involved in NASH Development

Figure 8:
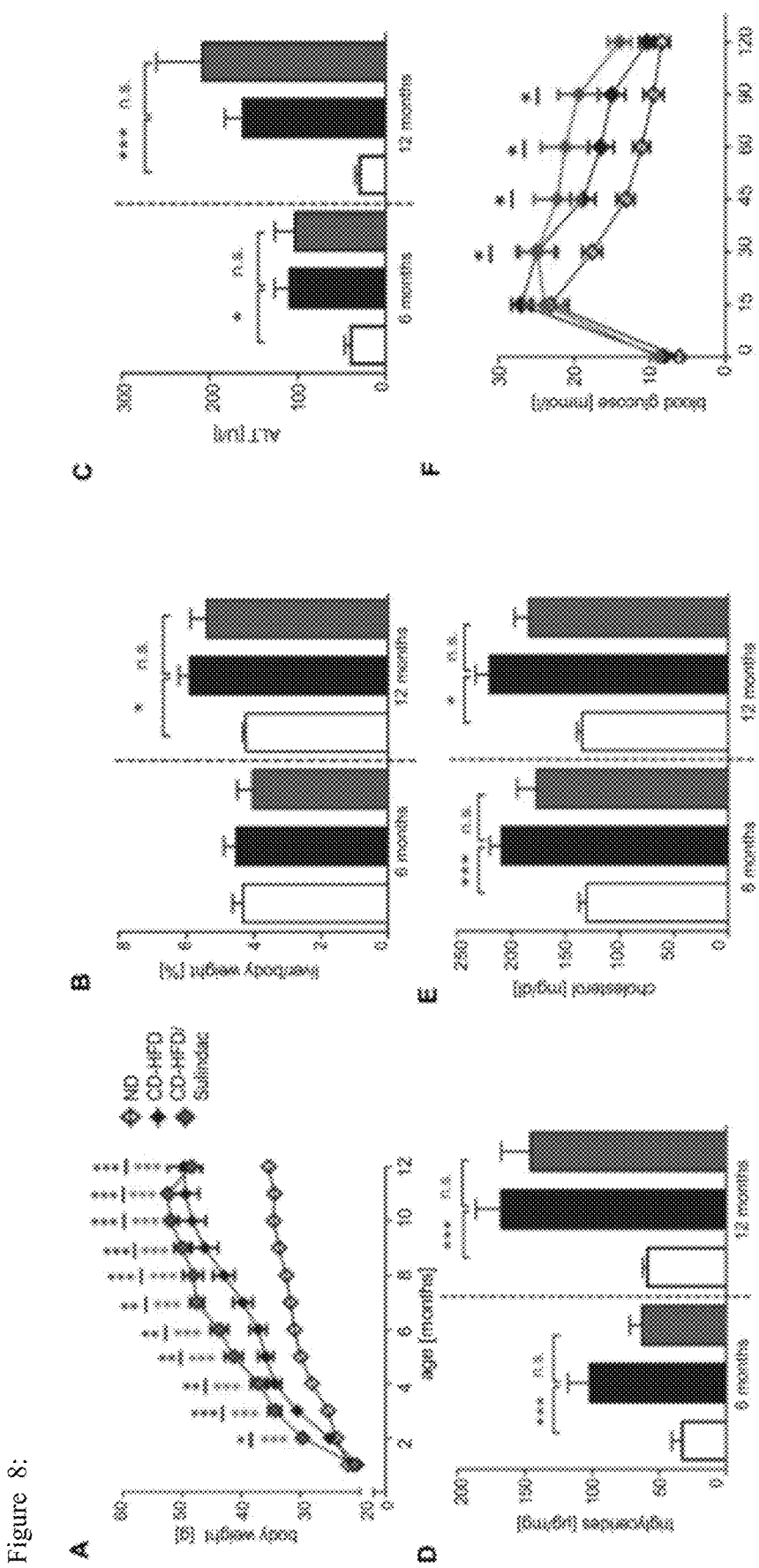
FIG. 8: COX1, COX2 inhibitor does not block steatosis or NASH development upon CD-HFD
Figure 8:
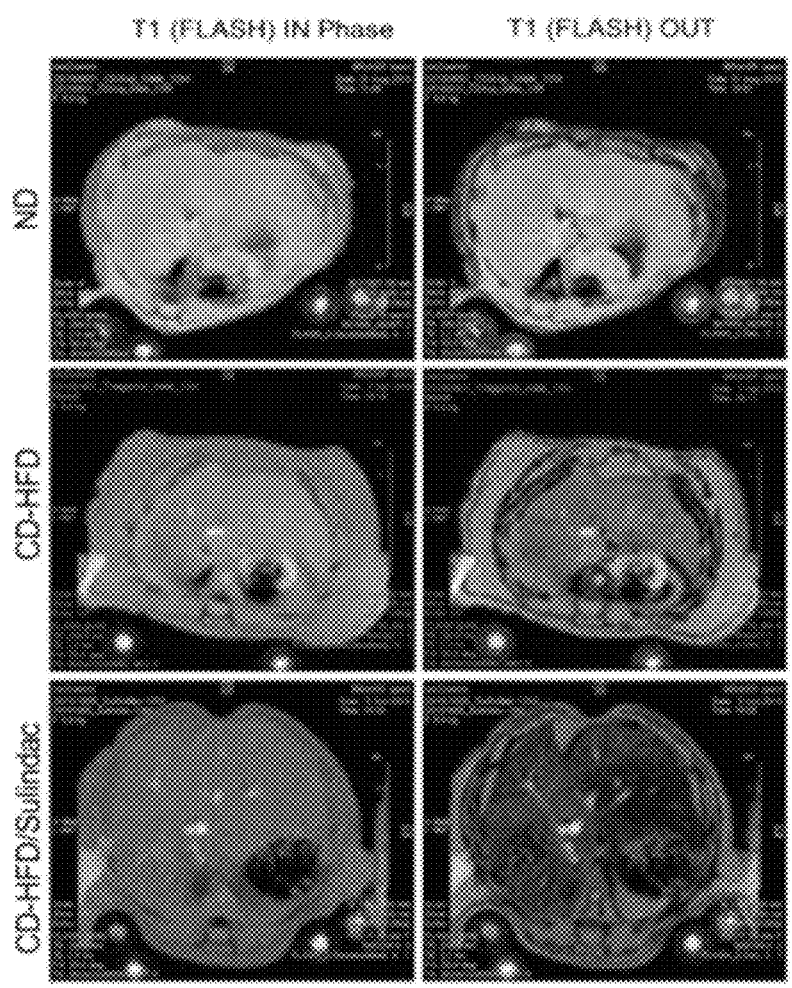
Figure 8:
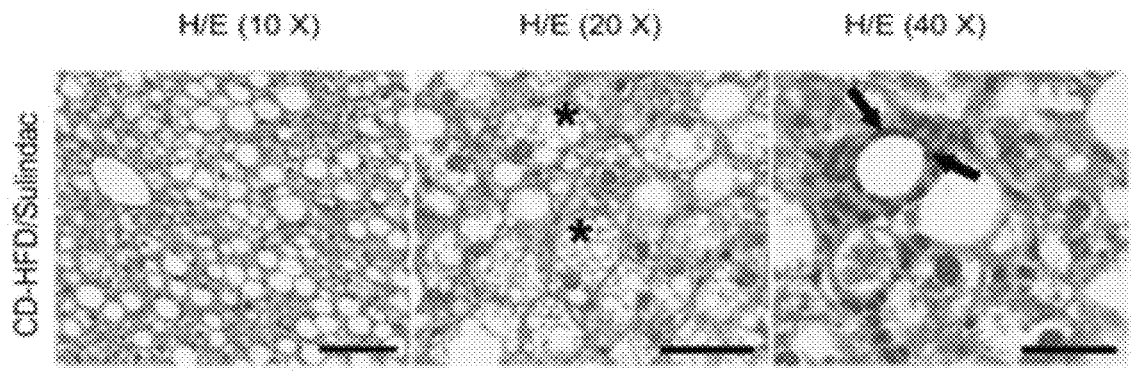
Figure 8:
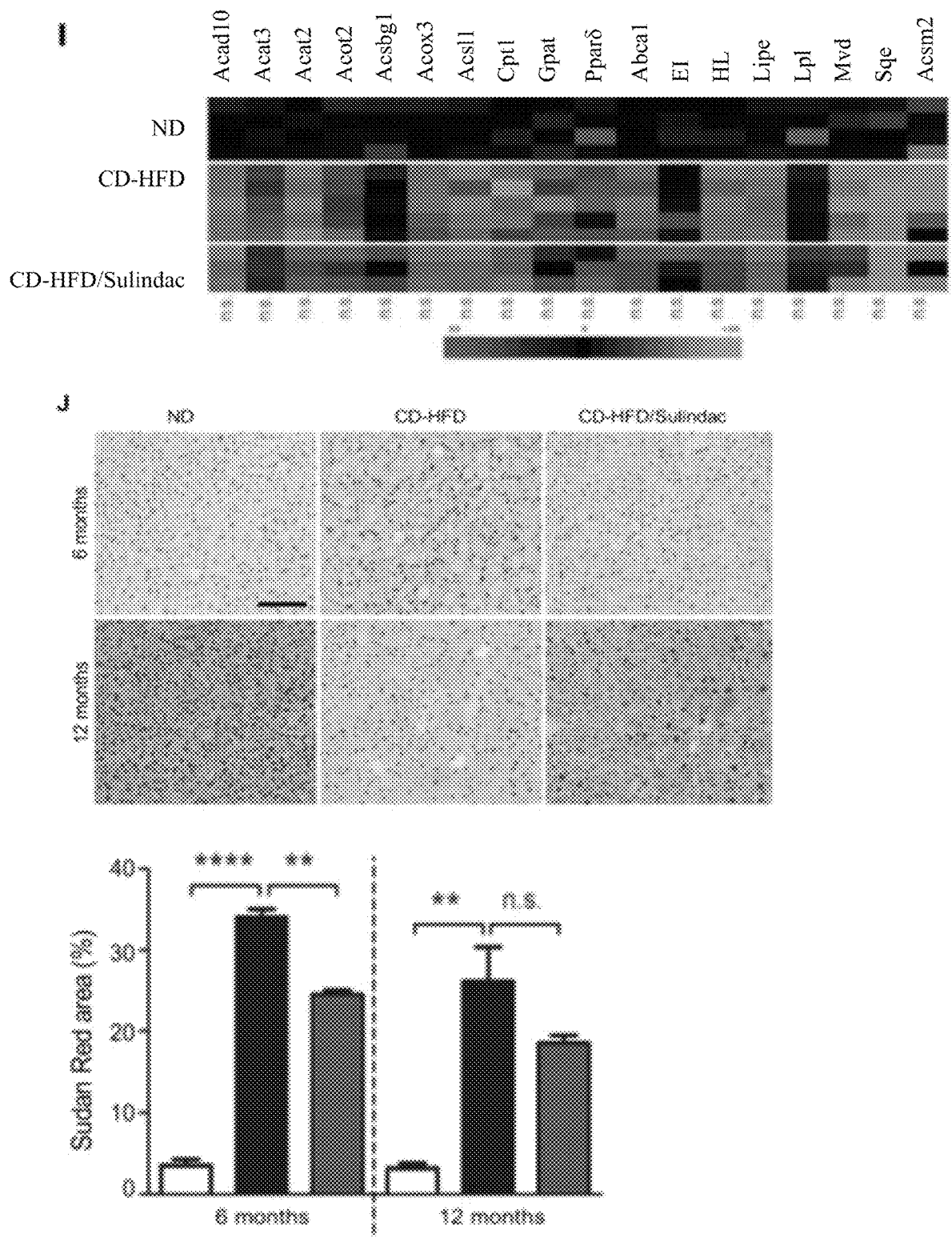

Sulindac, a COX1, COX2 inhibitor does not block steatosis or NASH development upon CD-HFD (FIG. 8). (FIG. 8A) CD-HFD fed mice do develop obesity as sulindac CD-HFD mice (White bars: ND; Black bars: CD-HFD; Red bars: CD-HFD treated with Sulindac). (FIG. 8B) Liver to body weight ratio is not rescued upon sulindac treatment at 12 months of age. (FIG. 8C) Liver damage as measured by ALT levels in serum is not prevented in sulindac treated mice. (FIG. 8D) Triglycerides are not significantly reduced in serum of sulindac treated mice at 6 or 12 months of age. (FIG. 8E) Serum cholesterol is not significantly reduced in Asp/Clop treated mice at 6 and 12 months, (FIG. 8F) Sulindac treated, CD-HFD fed mice are insulin resistant as CD-HFD fed mice, as investigated by an intraperitoneal glucose tolerance test. (FIGS. 8G and H) MRI analysis and histological analysis demonstrate that Sulindac treatment does not prevent the development of NASH. (FIG. 8G) Lipid deposition in the liver indicated by a dark staining in the T1 (FLASH) OUT phase is detected—as in the CD-HFD. At the same time abdominal and subcutaneous fat are visible in sulindac treated, CD-HFD fed mice as in CD-HFD fed mice alone. (FIG. 8H) Histopathological signs as indicated by H/E stains of NASH (e.g. ballooned hepatocytes—see also stars) are present in sulindac treated, CD-HFD fed mice. (FIG. 8I) Aberrant hepatic lipid metabolism and b-Oxidation is not rescued in sulindac treated mice—as analyzed by Real time PCR analysis for gene expression in the liver. Stars indicate significance. (FIG. 8J) Lipid deposition (as indicated by Sudan red) is not reduced in sulindac treated CD-HFD mice at 12 months, as indicated by histological and densitometric analysis.

Figure 9:
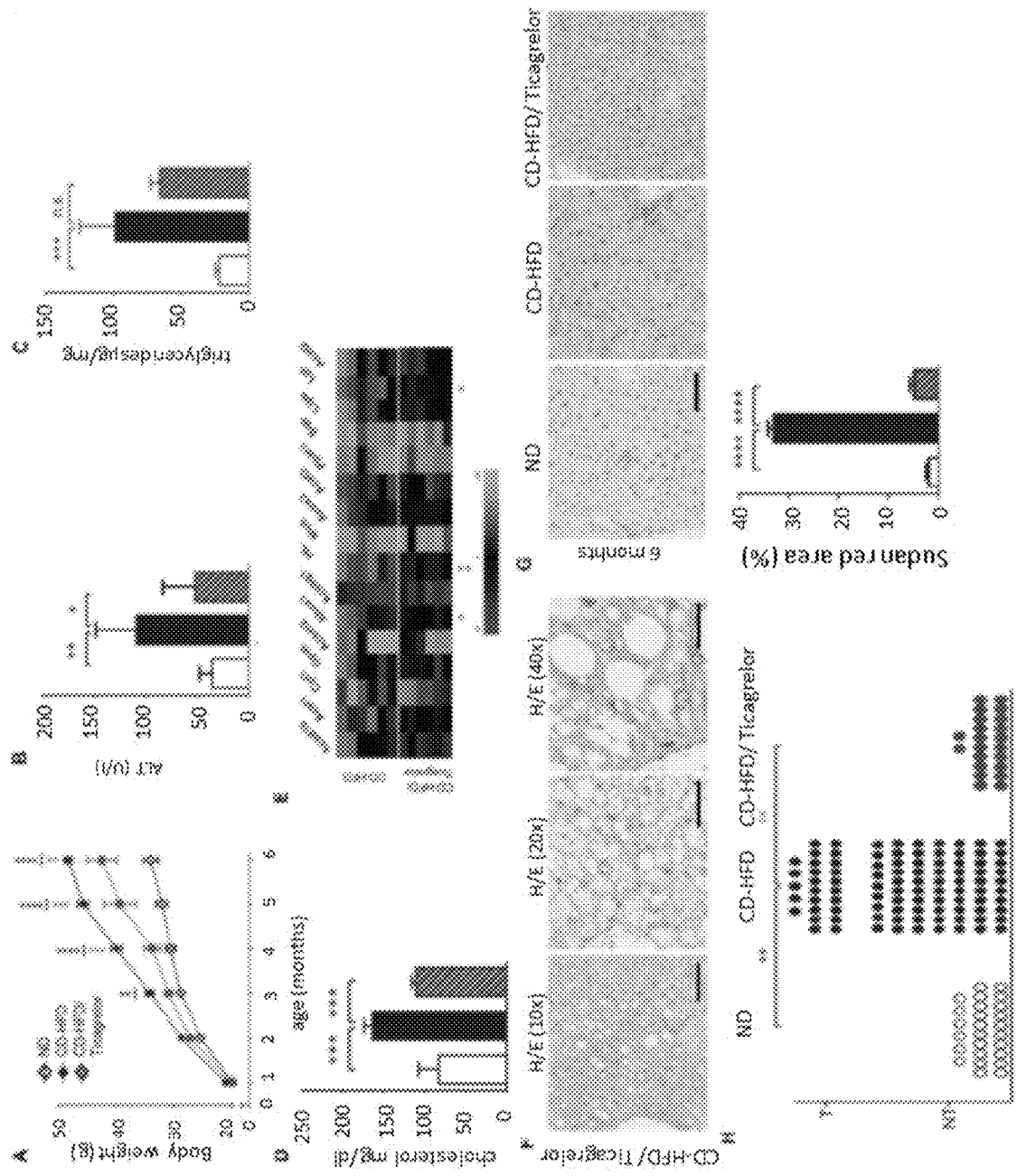
FIG. 9: Ticagrelor blocks NASH and HCC development

Example 5: The Platelet Aggregation Inhibitor Ticagrelor Inhibits NASH and HCC Development Ticagrelor blocks NASH and HCC development (FIG. 9). (FIG. 9A) CD-HFD fed mice do develop obesity as ticagrelor treated CD-HFD mice (White bars: ND; Black bars: CD-HFD; Green bars: CD-HFD treated with ticagrelor). (FIG. 9B) Liver damage as measured by ALT levels in serum is significantly reduced in ticagrelor treated mice. (FIG. 9C) Triglycerides are reduced by trend in serum of ticagrelor treated mice at 12 months of age. (FIG. 9D) Serum cholersterol is significantly reduced in ticagrelor treated mice at 6 and 12 months. (FIG. 9E) Aberrant hepatic lipid metabolism and b-Oxidation is rescued in ticagrelor treated mice—as analyzed by Real time PCR analysis for gene expression in the liver. Stars indicate significance. (FIG. 9F) Histopathological signs as indicated by H/E stains of NASH (e.g. ballooned hepatocytes—see also stars) are not present in ticagrelor treated, CD-HFD fed mice. (FIG. 9G) Lipid deposition (as indicated by Sudan red) is reduced in sulindac treated CD-HFD mice at 12 months, as indicated by histological and densitometric analysis. (FIG. 9H) No HCC in ticagrelor treated mice.

Example 6: Nbeal2 Knock-Out Inhibits NASH and Prevents HCC

Figure 10:
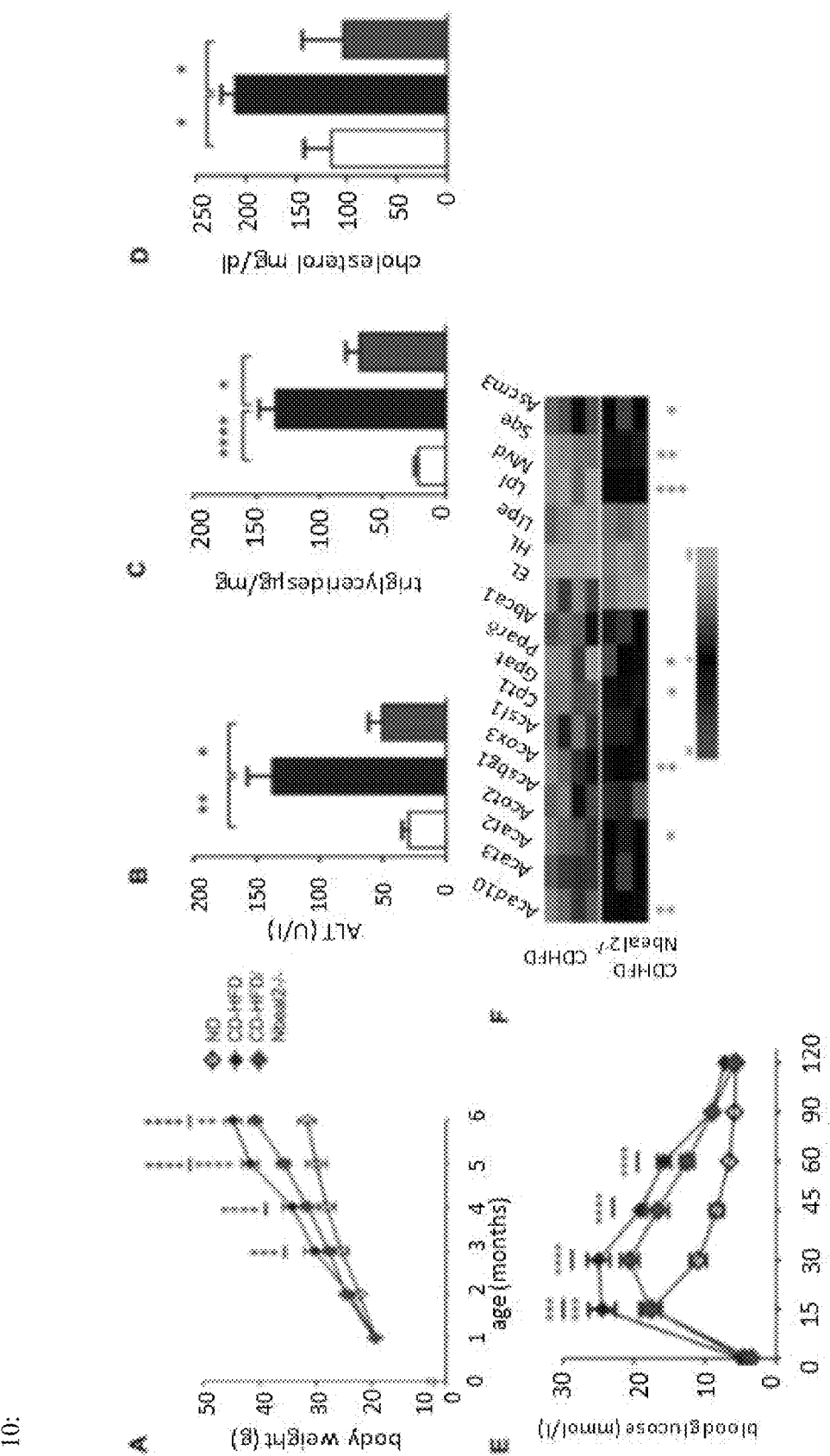
FIG. 10: Nbeal2−/− mice lack development of markers indicative of NASH development

Nbeal2−/− mice lack development of markers indicative of NASH development (FIG. 10). (FIG. 10A) CD-HFD fed C57BL/6 mice do develop obesity as CD-HFD fed Nbeal2−/− mice (White bars: ND; Black bars: CD-HFD; Blue bars: Nbeal2−/− mice on CD-HFD). (FIG. 10B) Liver damage as measured by ALT levels in serum is significantly reduced in CD-HFD fed Nbeal2−/− mice. (FIG. 10C) Triglycerides are significantly reduced in serum of CD-HFD fed Nbeal2−/− mice at 6 months of age. (FIG. 10D) Serum cholersterol is significantly reduced in CD-HFD fed Nbeal2−/− mice at 6 months. (FIG. 10E) CD-HFD fed Nbeal2−/− mice are insulin resistant as CD-HFD fed mice, as investigated by an intraperitoneal glucose tolerance test. (FIG. 10F) Aberrant hepatic lipid metabolism and b-Oxidation is partially rescued in CD-HFD fed Nbeal2−/− mice— as analyzed by Real time PCR analysis for gene expression in the liver. Stars indicate significance.

Example 7: Gp1b Knock-Out Inhibits NASH and Prevents HCC

Figure 11:
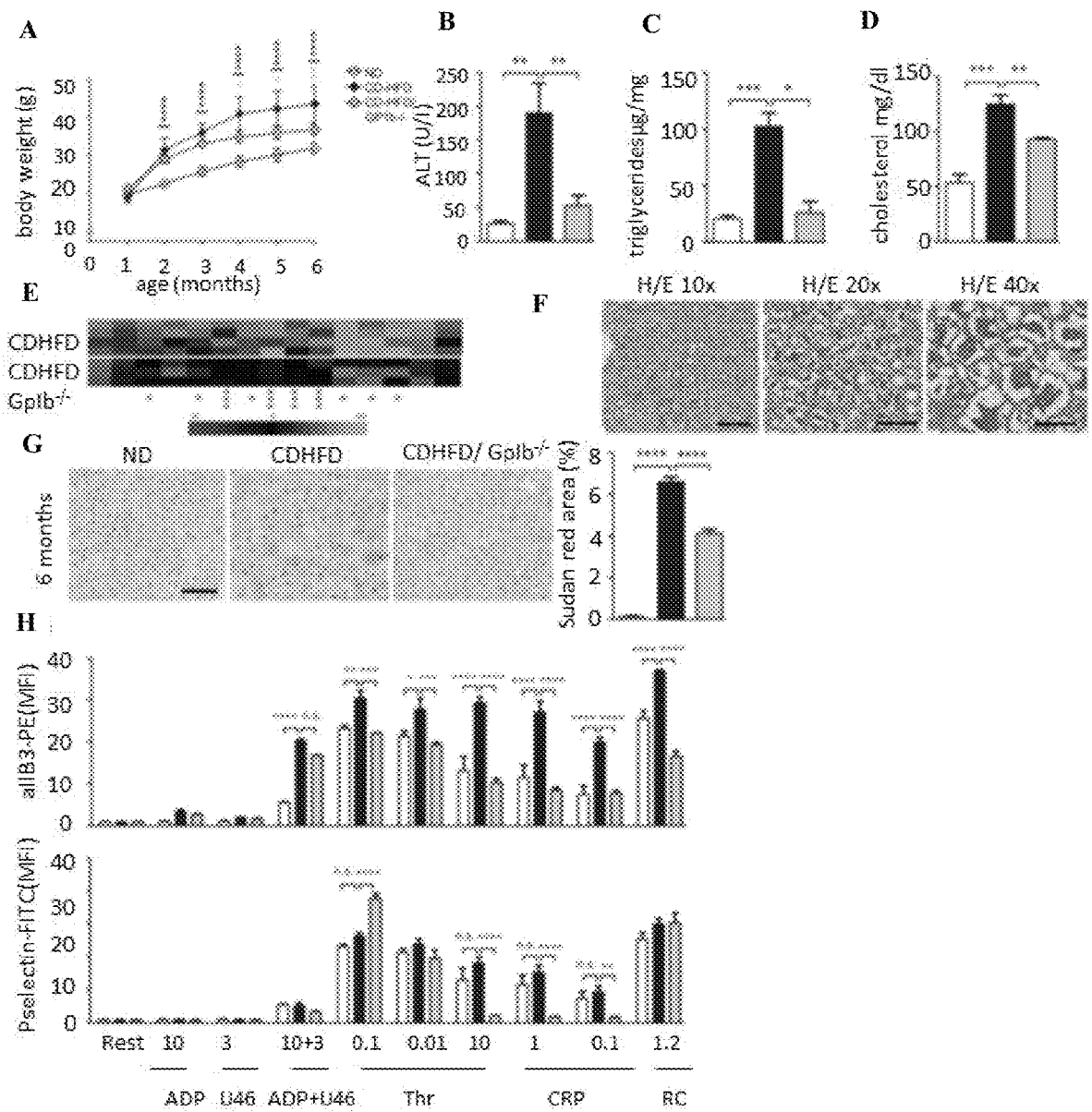
FIG. 11: GP1b−/− mice lack steatosis and NASH development

GP1b−/− mice lack steatosis and NASH development (FIG. 11). (FIG. 11A) CD-HFD fed C57BL/6 mice do develop obesity as CD-HFD fed Gp1b−/− mice (White bars: ND; Black bars: CD-HFD; yellow bars: Gp1b−/− mice on CD-HFD). (FIG. 11B) Liver damage as measured by ALT levels in serum is significantly reduced in CD-HFD fed Gp1b−/− mice. (FIG. 11C) Triglycerides are strongly reduced in serum of CD-HFD fed Gp1b−/− mice at 6 months of age. (FIG. 11D) Serum cholersterol is significantly reduced in CD-HFD fed Nbeal2−/− mice at 6 months. (FIG. 11E) Aberrant hepatic lipid metabolism and b-Oxidation is partially rescued in CD-HFD fed Gp1b−/− mice—as analyzed by Real time PCR analysis for gene expression in the liver. Stars indicate significance. (FIGS. 11F and G) Steatosis and NASH (e.g. ballooned hepatocytes) are gone in Gp1b−/− mice. Sudan red positive fatty droplets are quantified, corroborating our data. (FIG. 11H) Activation and aggregation capacity are significantly reduced upon ticagrelor treatment.

Example 8: Anti-Platelet Treatment in Humans

Figure 12:
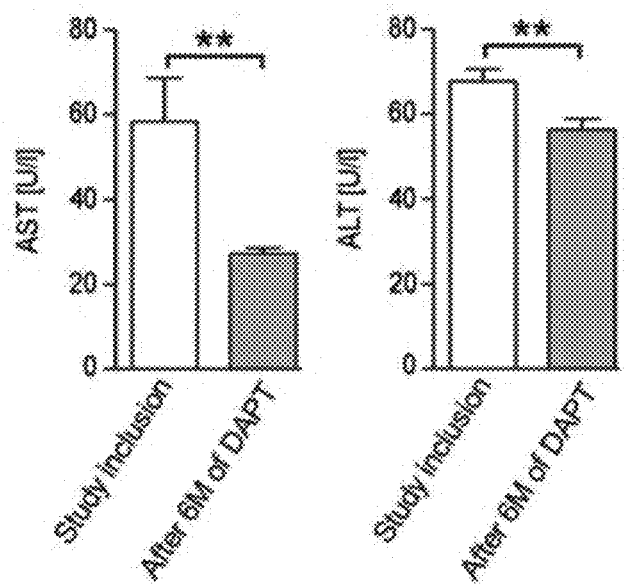
FIG. 12: Anti-platelet therapy in humans treats NASH and HCC
Figure 12:
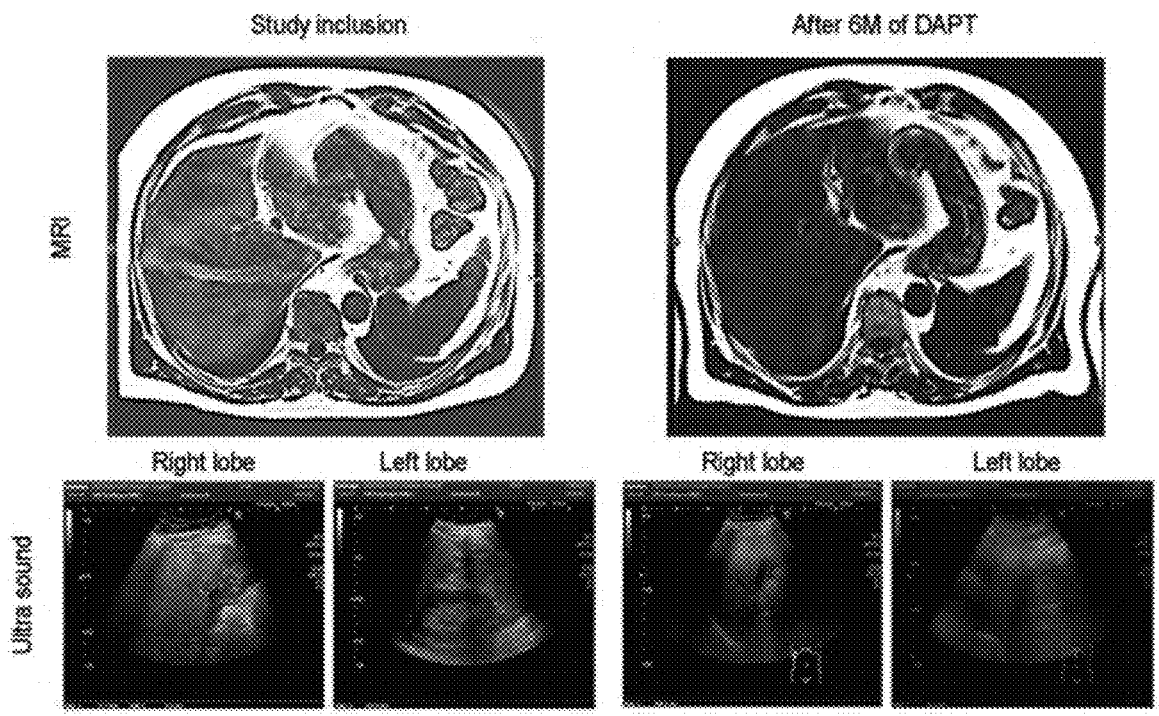
Figure 12:
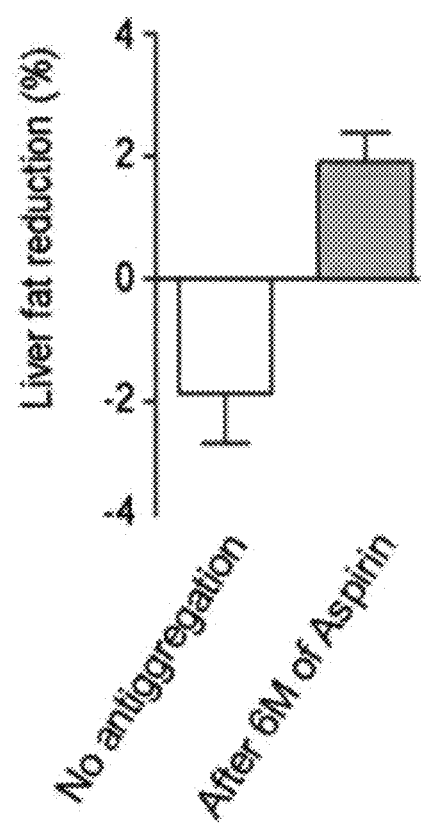

FIG. 12A shows enzymes aspartate transaminase (AST) and alanine transaminase (ALT) level of patients before study inclusion and after 6 months of dual-anti platelet therapy (DAPT) with Aspirin and Clopidogrel (n=148). FIG. 12 B shows an MRI and sonography of patients on ASA or DAPT before and 6 months after treatment. Quantification of liver fat deposition in human patients as assessed by MRI is shown in FIG. 12C. The experiment shows a significant effect of DAPT in the treatment of NASH.

Example 9: Anti Platelet Therapy Impairs Immune Cell Activity

Figure 13:
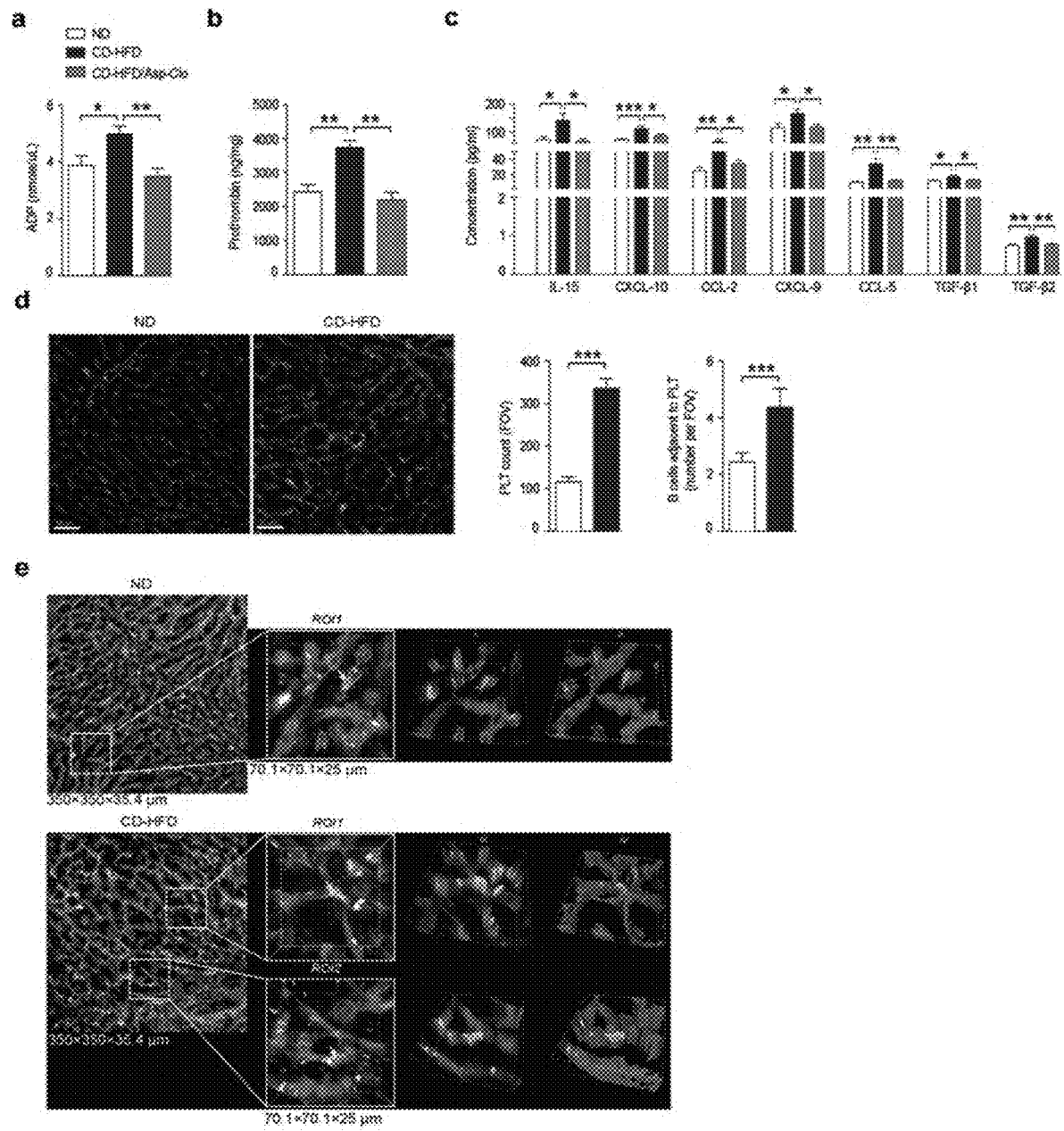
FIG. 13: Anti-platelet therapy reduces platelet activation/aggregation, cytokine release and platelet/immune cells interaction. (a) The level of ADP in the liver extract of mice under ND, CD-HFD and CD-HFD/Asp-Clo. (data were pooled from two different independent experiments (n=10 mice per each group). *P<0.05, P<0.01, Student's t-test. (b) Prothrombin measured by enzyme-linked immunosorbent assay (ELISA) in mouse liver extract extracts from different groups (representative of two independent experiments (n=5 mice per group). P<0.01 determined by Student's t-test. (c) Analysis of cytokines in the liver extracts. Normalized amount of liver protein extracts were analyzed in ND, CD-HFD and Asp-Clo treated CD-HFD fed mice. (data are pooled from two independent experiments, n≥10 per each group). Significance was determined by Student's t-test, *P<0.05,P<0.01, *P<0.001. (d) Representative confocal micrographs and quantification of the platelet/B-cell interaction in the liver of ND, CD-HFD fed and CD-HFD fed treated with Asp-Clo mice (n=4 mice per group) are shown. Sinusoids are presented in blue, platelets are presented in green and B-cells are presented in red. Scale bar represents 50 μm. Platelet count alone and platelet adjacent to B-cells quantification are shown in focus of view (FOV) (n=4 mice per group). For visualization of intravascular events and to increase image clarity, the transparency of the sinusoidal rendering was set to 50%. See also Movie S3 and Movie S4. (e) Representative confocal images from the liver of ND, CD-HFD fed mice and also Asp-Clo treated CD-HFD fed mice for platelet/CD8$^+$ T cells interaction in region of interest (ROI), the same mice visualized for (d). Sinusoids are presented in blue, platelets are presented in green and CD8$^+$ T cells are presented in red. Scale bar represents 50 μm. Single platelet count as well as platelet/CD8$^+$ T cell quantification are shown in focus of view (FOV) (the same mice used for (d). For a-e, a two-tailed unpaired Student's t-test was used for statistical analysis: *P<0.05, P<0.01, *P<0.001.

Anti platelet therapy reduces chemokines and cytokines in the liver, reduces ADP levels and prothrombin levels as shown in FIG. 13 A-C. Further it was observed that anti-platelet therapy reduces immune cells in the liver by blocking platelet immune cell interaction (FIGS. 13 D and E).

The invention claimed is:

1. A method for the treatment of non-alcoholic steatohepatitis (NASH), wherein said method comprises administering, to a subject in need of such treatment, an inhibitor of thrombocyte aggregation or activation, wherein the inhibitor is an antisense nucleotide sequence that binds to Gp1b and modulates Gp1b expression.

2. The method according to claim 1, wherein the treatment is an alleviation or a reduced progression of NASH.

3. The method according to claim 1, wherein the treatment is a reduced, stalled, or reversed progression of NASH into liver cirrhosis.

4. The method according to claim 1, wherein the treatment is a prevention of HCC in a NASH-patient at risk to develop cirrhosis and/or HCC.

5. The method according to claim 1, wherein the treatment is performed in a patient at risk of developing NASH, wherein the patient is a diabetic patient, an obese patient, or a patient suffering from metabolic syndrome or from another metabolic disorder.

6. The method according to claim 1, wherein the subject to be treated does not have a condition selected from the group consisting of alcoholic liver injury, drug-induced liver injury, chronic active hepatitis, hepatic steatosis and hepatocyte apoptosis.

7. The method according to claim 1, wherein the antisense nucleotide sequence is a LNA-construct.

8. The method according to claim 1, wherein the treatment is a reduced, stalled, or reversed progression of NASH into hepatocellular carcinoma (HCC).

9. The method, according to claim 6, wherein the patient suffers from an inflamed fatty liver.

10. The method according to claim 1, wherein the antisense nucleotide sequence comprises a sequence complementary to a Gp1b mRNA sequence.

11. The method according to claim 1, wherein the antisense nucleotide sequence is an RNA interference inducing nucleotide sequence.

* * * * *